United States Patent [19]

Rico et al.

[11] 4,377,711
[45] Mar. 22, 1983

[54] NOVEL AROMATIC BROMOPOLYFLUOROALKYL ETHERS AND METHOD FOR THE PREPARATION THEREOF

[75] Inventors: Isabelle Rico, Paris; Claude Wakselman, Villebon-sur-Yvette, both of France

[73] Assignee: Rhone-Poulenc Industries, Paris, France

[21] Appl. No.: 318,147

[22] Filed: Nov. 4, 1981

[51] Int. Cl.³ .......................................... C07C 43/205
[52] U.S. Cl. ........................ 568/588; 568/655; 568/656; 568/637; 568/642; 568/649; 564/176; 564/442
[58] Field of Search ............... 568/588, 655, 656, 637, 568/642, 649; 564/176, 442

[56] References Cited

U.S. PATENT DOCUMENTS

| | | | |
|---|---|---|---|
| 2,108,606 | 2/1938 | Muller et al. | 260/142 |
| 2,754,334 | 7/1956 | Bahner | 260/609 |
| 3,277,068 | 10/1966 | Wall et al. | 568/655 X |
| 3,576,882 | 4/1971 | Clark | 260/609 |
| 3,714,233 | 1/1973 | Larsen et al. | 260/479 |
| 4,014,891 | 3/1977 | Goralski et al. | 260/302 |
| 4,030,911 | 6/1977 | Arneklev et al. | 71/98 |
| 4,093,665 | 6/1978 | Belous et al. | 568/656 X |
| 4,157,344 | 6/1979 | Feiring | 568/588 X |

OTHER PUBLICATIONS

Morrison et al., Organic Chemistry (1959), pp. 588–589.
Advances in Fluorine Chemistry, vol. 3 (1963), pp. 181–270.
Yagupolskii, Chem. Abs., vol. 50 (1956), 11270b.
Yarovenko et al., Chem. Abs., vol. 53 (1959), 3116i.
Banks, Organofluorine Chemicals and Their Industrial Applications (1979), pp. 62–78.
Chem. Abstracts, vol. 81, 104876d (1974).
Feiring, Andrew E., "Chemistry in Hydrogen Fluoride, 7, A Novel Synthesis of Aryl Trifluoromethyl Ethers," *J. Org. Chem.*, vol. 44, No. 16, pp. 2907–2910 (1979).
Rico, Isabelle, et al., "Synthese De Composes Aromatiques Comportant Les Groupements OCF₂Br Et SCF₂Br," *Tetrahedron Letters*, vol. 22, pp. 323–326 (Jan. 1981).

*Primary Examiner*—Bernard Helfin

[57] ABSTRACT

Disclosed are aromatic bromopolyfluoroalkyl ethers of the formula:

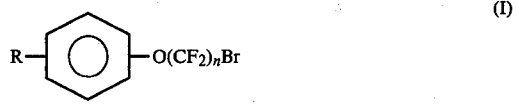

where n is equal to 1 or 2 and R represents at least one moiety selected from the group consisting of hydrogen, the alkyl radicals having from 1 to 12 carbon atoms, the phenyl radical, the alkoxy radicals having from 1 to 12 carbon atoms, the phenyloxy radical, and the radicals $NO_2$, CN, Cl, F, Br, I, $CF_3$, and $CONR_1R_2$ and $NR_1R_2$ where $R_1$ and $R_2$ are identical or different and represent each a hydrogen or an alkyl radical having from 1 to 6 carbon atoms. Also disclosed is a method for preparation of these ethers. These compounds are useful as intermediates in producing products exhibiting phytosanitary or pharmaceutical activity.

17 Claims, No Drawings

NOVEL AROMATIC BROMOPOLYFLUOROALKYL ETHERS AND METHOD FOR THE PREPARATION THEREOF

BACKGROUND OF THE INVENTION

The present invention relates to aromatic bromopolyfluoroalkylethers. The invention also relates to a method for their preparation.

SUMMARY OF THE INVENTION

The novel aromatic compounds in accordance with the present invention have the general formula:

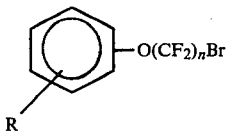
(I)

where:

n is equal to 1 or 2 and R represents at least one moiety chosen from the group consisting of hydrogen, the alkyl radicals having from 1 to 12 carbon atoms, the phenyl radical, the alkoxy radicals having from 1 to 12 carbon atoms, the phenyloxy radical, and the radicals $NO_2$, CN, F, Cl, Br, I, $CF_3$, and $CONR_1R_2$ and $NR_1R_2$ where $R_1$ and $R_2$ are identical or different and represent each a hydrogen or an alkyl radical having from 1 to 6 carbon atoms.

The compounds of formula I can be used as synthesis intermediates for the preparation of products having phytosanitary or pharmaceutical activity. Through halogen exchange the compounds of this invention yield corresponding perfluoroalkylethers, which are intermediates that are well known for the synthesis of the aforesaid products.

The invention also relates to a method for the preparation of the compounds of formula I, said method characterized in that a bromine compound of the formula:

$Br(CF_2)_n—X$ (II)

where X represents chlorine or bromine and n is equal to 1 or 2 is reacted with a phenate of the formula:

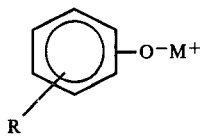
(III)

where R has the same meaning as above and where $M^+$ represents a cation derived from an alkaline metal. The reaction is carried out in an anhydrous polar aprotic solvent in the presence of a thiol reaction initiator.

DETAILED DESCRIPTION OF THE INVENTION

According to a preferred mode, the compound of formula II is $Br(CF_2)_nBr$, which makes it possible to obtain optimum results. To obtain improved yields, it is preferable to use a potassium phenate as the compound of formula III. With it, the amount of by-product produced (corresponding compound containing the $—O(CF_2)_nH$ group) is minimized.

The polar aprotic solvent is preferably a solvent whose dielectric constant is greater than 15, for example, dimethylformamide, dimethylacetamide, dimethylsulfoxide, hexamethylenephosphorotriamide, N-methylpyrrolidone, and sulfolane. The solvent used must be aprotic to prevent formation of the by-product containing the $—O(CF_2)_nH$ group and it must be polar to enhance the reactivity of the phenate. The preferred solvent is dimethylformamide.

To initiate the reaction, it is necessary to add a thiol to the reaction medium. The thiol can be represented by the formula $R_3SH$. Because the reaction medium is basic, the thiol liberates the $R_3S^-$ ion, whose nucleophilic nature makes the reaction initiation possible. $R_3$ may represent any organic hydrocarbon radical (alkyl or aryl) or one that contains hetero atoms. The alkane thiols, such as ethane thiol, propane thiol, butane thiol, the thiophenols, and the benzyl mercaptans may be used. Propane thiol is preferred because the by-products formed with its use are sufficiently volatile to be readily eliminated.

The thiol is used in such an amount that the molar ratio of the thiol to the phenate is from approximately 0.05/1 to approximately 0.2/1. Preferably, this ratio is from 0.07/1 to 0.15/1.

The compounds of formulas II and III are preferably used in such amounts that the molar ratio of the formula II compound to the formula III compound is from approximately 1/1 to approximately 5/1. Preferably, this ratio is from approximately 1/1 to approximately 3/1.

The solvent is used in such an amount that the number of moles of phenate per liter of solvent is from approximately 0.1/1 to approximately 0.5/1 and preferably from 0.15/1 to 0.3/1.

The reaction is carried out at a temperature from approximately 20° to 100° C. and preferably from 20° to 60° C. Operation is usually at atmospheric pressure but pressures higher or lower may be used. Generally, the reaction time is from 3 to 12 hours.

It is desirable to use a solvent from which gas has been removed, that is, a solvent free particularly from oxygen (from the air) and to maintain agitation of the reaction medium. It is also desirable to use an anhydrous phenate. Thus, it is desirable to dry the phenate before reaction. The presence of water in the reaction medium promotes the formation of the corresponding by-product containing the $—O(CF_2)_nH$ group.

The compounds of formulas II and III may be prepared according to the methods well known to those skilled in the art.

The following examples are provided for illustrative purposes only and should not be construed to limit the scope of the invention.

EXAMPLE 1

Preparation of bromodifluoromethoxy,methyl-4 benzene

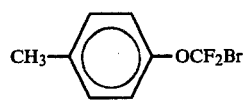

by the action of CF₂Br₂ on

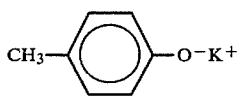

In a flask fitted with a dry ice (solid CO₂) condenser and containing 400 ml of anhydrous dimethylformamide from which gas was removed with argon, 14.6 g (0.1 mole) of

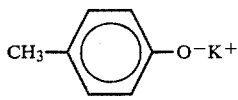

and 0.76 g (0.01 mole) of propane thiol are dissolved at 20° C. Drop by drop, accompanied by stirring, 42 g (0.2 mole) of CF₂Br₂ are added. The temperature rises from 20° to 30° C. Stirring is continued for four hours at ambient temperature. The solvent and the KBr that is being formed during the reaction are removed through the addition of 400 ml of water acidified by HCl (at 17%). The decanted oil is recovered. Following purification by steam distillation, the oil is dried with sodium carbonate. Using "revolving band" distillation, 5 g of a product is recovered. The product's boiling point at 34 mm Hg is 90° C. and NMR (nuclear magnetic resonance) analysis of the proton and of the fluorine indicates the product's formula is

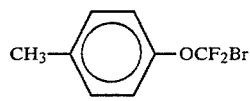

EXAMPLE 2

Preparation of bromodifluoromethoxy,methyl-4 benzene

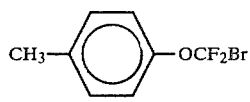

by the action of CF₂BrCl on

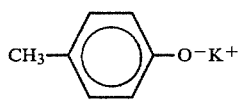

In a flask fitted with a dry ice condenser and containing 400 ml of anhydrous dimethylformamide from which gas was removed with argon, 14.6 g (0.1 mole) of

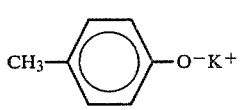

and 0.76 g (0.01 mole) of propane thiol are dissolved at 20° C. In one addition 33 g (0.2 mole) of CF₂BrCl that have previously been condensed in an acetone/dry ice bath are added. The temperature rises by a few degrees. The procedure of Example 1 is then followed. By "revolving band" distillation 2.8 g of:

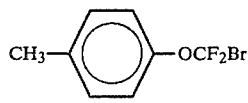

are recovered.

EXAMPLE 3

Preparation of bromodifluoromethoxybenzene

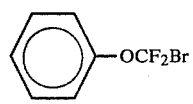

by the action of CF₂Br₂ on

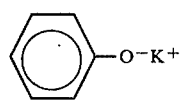

The procedure of Example 1 is used but with 13.2 g (0.1 mole) of:

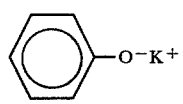

Through "revolving band" distillation, 2 g of a product are obtained. Its boiling point at 34 mm Hg is 70° C. and its NMR analysis of the proton and of the fluorine indicates the product's formula is

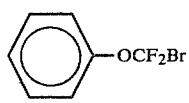

EXAMPLE 4

Preparation of bromodifluoromethoxy,chloro-4 benzene

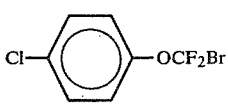

by the action of CF₂Br₂ on

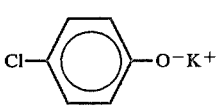

The procedure of Example 1 is used but with 16.6 g (0.1 mole) of:

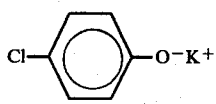

Through "revolving band" distillation, 4.1 g of a product are obtained. Its boiling point at 32 mm Hg is 94° C. and its NMR analysis of the proton and of the fluorine indicates the product's formula is

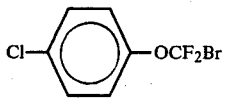

EXAMPLE 5

Preparation of bromodifluoromethoxy,nitro-4 benzene

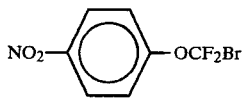

by the action of $CF_2Br_2$ on

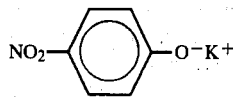

The procedure of Example 1 is used but with 17.7 g (0.1 mole) of:

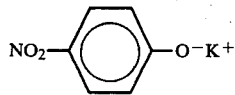

By chromatography on a silica plate (using benzene as the eluent) 6.7 g of a product are recovered. Its melting point is 48° C. and its NMR analysis of the proton and of the fluorine indicates the product's formula is

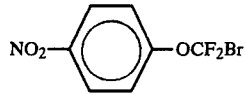

EXAMPLE 6

Preparation of beta-bromotetrafluoroethoxymethyl-4 benzene

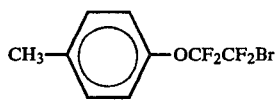

by the action of $BrCF_2CF_2Br$ on

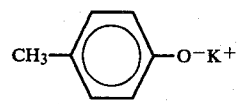

In a flask fitted with a dry ice condenser and containing 400 ml of anhydrous dimethylformamide from which gas was removed with argon, 14.6 g (0.1 mole) of:

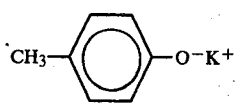

and 0.76 g (0.01 mole) of propane thiol are dissolved at 20° C. Drop by drop, accompanied by stirring, 39 g (0.15 mole) of $BrCF_2CF_2Br$ are added. The temperature rises from 20° to 24° C. Stirring is continued for 1 hour at 40° C. and then for 12 hours at ambient temperature. The solvent and the KBr that is being formed during the reaction are removed through the addition of 400 ml of water acidified by HCl (at 17%). The oil that is decanted is recovered. Following purification by steam distillation, this oil is dried with sodium carbonate. Using "revolving band" distillation, 10.9 g of a product are recovered. Its boiling point at 30 mm Hg is 86° C. and its NMR analysis of the proton and of the fluorine indicates the product's formula is

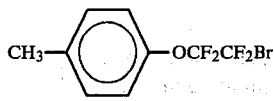

EXAMPLE 7

Preparation of beta-bromotetrafluoroethoxybenzene

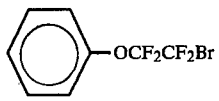

by the action of $BrCF_2CF_2Br$ on

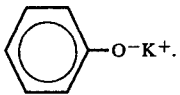

The procedure of Example 6 is used but with 13.2 g (0.1 mole) of

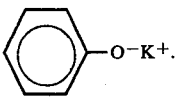

By "revolving band" distillation, 7 g of a product are obtained. Its boiling point at 40 mm Hg is 76° C. and its NMR analysis of the proton and of the fluorine indicates the product's formula is

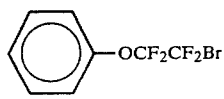

EXAMPLE 8

Preparation of beta-bromotetrafluoroethoxy, chloro-4 benzene

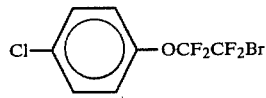

by the action of BrCF$_2$CF$_2$Br on

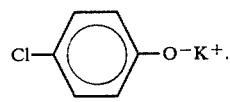

The procedure of Example 6 is used but with 16.6 g (0.1 mole) of

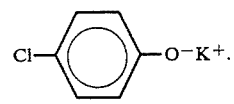

By "revolving band" distillation, 5.8 of a product are obtained. Its boiling point at 30 mm Hg is 80° C. and its NMR analysis of the proton and of the fluorine indicates the product's formula is

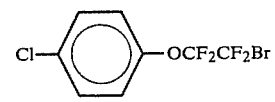

EXAMPLE 9

Preparation of beta-bromotetrafluoroethoxy, nitro-4 benzene

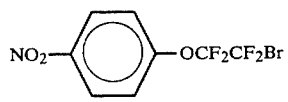

by the action of BrCF$_2$CF$_2$Br on

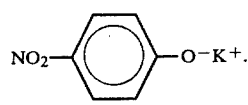

The procedure of Example 6 is used but with 17.7 g (0.1 mole) of

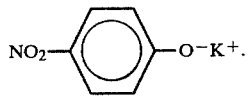

By chromatography on a silica plate (using benzene as the eluent), 2 g of a product are obtained. Its melting point is 65° C. and its NMR analysis of the proton and of the fluorine indicates the product's formula is

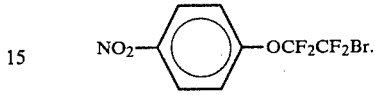

Variations and modifications will be obvious to one skilled in the art and the claims are intended to cover all variations and modifications that fall within the true spirit and scope of the invention.

We claim:

1. Aromatic bromopolyfluoroalkylethers of the formula:

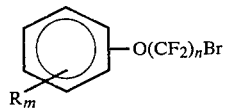

(I)

where n is equal to 1 or 2; m is equal to 1, 2, 3, or 4; and R represents at least one moiety selected from the group consisting of hydrogen, the alkyl radicals having from 1 to 12 carbon atoms, the phenyl radical, the alkoxy radicals having from 1 to 12 carbon atoms, the phenyloxy radical, and the radicals NO$_2$, CN, Cl, F, Br, I, CF$_3$, CONR$_1$R$_2$ and NR$_1$R$_2$ where R$_1$ and R$_2$ are identical or different and represent each a hydrogen or an alkyl radical having from 1 to 6 carbons atoms.

2. An aromatic bromopolyfluoroalkylether according to claim 1, having the formula:

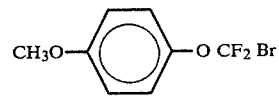

3. An aromatic bromopolyfluoroalkylether according to claim 1, having the formula:

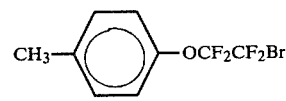

4. Aromatic bromopolyfluoroalkylethers according to claim 1, having the formula:

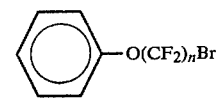

5. Aromatic bromopolyfluoroalkylethers according to claim 1, having the formula:

6. Aromatic bromopolyfluoroalkylethers according to claim 1, having the formula:

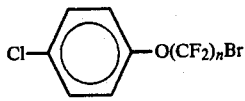

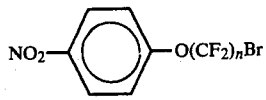

7. A process for preparing the compounds of claim 1, characterized in that a bromine compound having the formula:

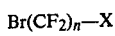

$$Br(CF_2)_n-X \qquad (II)$$

where X represents chlorine or bromine and n is equal to 1 or 2 is reacted with a phenate of the formula:

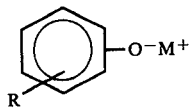

where R is as defined in claim 1 and $M^+$ represents a cation derived from an alkaline metal, said reaction being carried out in an anhydrous polar aprotic solvent in the presence of a thiol reaction initiator.

8. A process according to claim 7, characterized in that in the bromine compound, X=Br.

9. A process according to claim 7, characterized in that in the phenate, $M^+$ represents the cation derived from potassium.

10. A process according to claim 7, characterized in that the polar aprotic solvent is chosen from the group consisting of dimethylformamide, dimethylsulfoxide, hexamethylenephosphorotriamide N-methylpyrrolidone, and sulfolane.

11. A process according to claim 10, characterized in that the solvent is dimethylformamide.

12. A process according to claim 7, characterized in that the thiol is chosen from the group consisting of alkane thiols, thiophenols, and benzylmercaptans.

13. A process according to claim 12, characterized in that the thiol is propane thiol.

14. A process according to claim 7, characterized in that the molar ratio of the thiol to the phenate is from approximately 0.05/1 to approximately 0.2/1.

15. A process according to claim 7, characterized in that the molar ratio of the bromine compound to the phenate is from approximately 1/1 to approximately 5/1.

16. A process according to claim 7, characterized in that the number of moles of phenate per liter of solvent is from approximately 0.1 to approximately 0.5.

17. A process according to any one of claims 7 to 16, characterized in the temperature of reaction is from approximately 20° to approximately 100° C. and the pressure is atmospheric.

* * * * *